United States Patent [19]

Oden

[11] Patent Number: 5,580,857
[45] Date of Patent: Dec. 3, 1996

[54] USE OF GIBBERELLINS FOR THE TREATMENT OF PROSTATITIS

[76] Inventor: Per Oden, Motorbåtsvägen 38, S-902 91 Täfteå, Sweden

[21] Appl. No.: 185,286

[22] Filed: Jan. 24, 1994

Related U.S. Application Data

[63] Continuation of Ser. No. 854,615, filed as PCT/SE90/00815, Dec. 10, 1990, published as WO91/08751, Jun. 27, 1991, abandoned.

[30] Foreign Application Priority Data

Dec. 12, 1989 [DK] Denmark .................................. 6262/89

[51] Int. Cl.⁶ .......................... A61K 31/70; A61K 31/19; A61K 31/11; C07H 15/00
[52] U.S. Cl. .................. 514/25; 514/33; 514/34; 514/468; 514/557; 514/569; 514/574; 514/577; 514/691; 514/693; 514/700; 514/703; 514/705; 514/738; 514/739; 536/16.8; 536/18.1; 536/18.2
[58] Field of Search .................. 536/18.1, 18.2, 536/16.8; 514/25, 33, 34, 557, 569, 574, 577, 691, 693, 700, 703, 705, 738, 739, 468

[56] References Cited

U.S. PATENT DOCUMENTS

| | | | |
|---|---|---|---|
| 4,381,402 | 4/1983 | DuBois | 536/18.1 |
| 4,434,232 | 1/1984 | Parkinson | 514/458 |
| 4,454,290 | 6/1984 | DuBois | 536/18.1 |
| 4,518,614 | 5/1985 | Parkinson | 514/458 |

FOREIGN PATENT DOCUMENTS

WO84/01710  5/1984  WIPO.

OTHER PUBLICATIONS

D. H. Davis et al, "Aloe Vera and Gibberellin, Anti–Inflammatory Activity in Diabetes" Dialog Information Services, File 154: Medline 83–90/Sep., Dialog Accession No. 06956381.

A. M. Gawienowski, "Androgenic Properties of Gibberellic Acid in the Chick Comb Bioassay", Experientia 33/11, pp. 1544–1545.

A. Inczefi–Gonda et al, "Effect of a Single Neonatal Treatament with Steroid Hormone or Steroid–like Molecules on Myocardial Ouabain Binding in the Adult Rat" Gen. Physiol. Biophys. 1987.6.279–283.

A. Miklussak et al, "Application of Gibberelie Acid (GA) Alone or Together with Cytostatics in Treatment of Lung Cancer", pp. 203–209.

S. L. Vesely et al, "Gibberellic Acid, A Plant Growth Hormone, Enhances Mammalian Guyanylate Cyclase Activity", Research Communications in Chemical Pathology and Pharmacology, vol. 28, No. 1 Apr. 1990.

Robert H. Davis et al, "ALoe Vera and Gibberelin: Anti–Inflammatory Activity in Diabetes", Journal of the Americal Podiatric Medical Association, pp. 24–26.

Par C. Bouton, et al, "Etude de L'action de l'acide gibberelique chez le rat male adulte castre" Societe de Biologe. pp. 1302–1306.

E. Schwatz et al, "Pharmakologische Wirkungen der Gibberellinsaure" Pharamazie 38, 1983, pp. 716–718.

The Merck Manual; 16th Ed. pp. 1715–1716, 1736–1737; 2435–2436 (1992).

Primary Examiner—Douglas W. Robinson
Assistant Examiner—Howard C. Lee
Attorney, Agent, or Firm—Lowe, Price, Leblanc & Becker

[57] ABSTRACT

The use of active gibberellins for the preparation of a pharmaceutical composition for the treatment of prostatitis. The method results in a decrease in prostate mass.

20 Claims, No Drawings

USE OF GIBBERELLINS FOR THE TREATMENT OF PROSTATITIS

This application is a continuation of application Ser. No. 07/854,615 filed as PCT/SE90/00815 Dec. 10, 1990 published as WO91/08751 Jun. 27, 1991 now abandoned.

FIELD OF THE INVENTION

The present invention relates to the use of the group of compounds known as gibberellins for the preparation of a pharmaceutical composition for the treatment of prostatitis, including hypertrophy and hyperplastic adenoma of the prostate, and psoriasis, as well as a method for treating these and other conditions by administering a gibberellin or a pharmaceutically acceptable salt or lactones thereof.

BACKGROUND OF THE INVENTION

The gibberellins are a group of compounds which are found in plants and certain fungi. Gibberellins are plant growth regulators (phytohormones), stimulating growth and differentiation of plants in very small amounts. About 75 different gibberellins have been isolated and described.

Gibberellins are weak acids with a ring system containing double bonds and 8 asymmetric carbons, and can be synthesized from the tetracyclic diterpenoid carbohydrate ent-kaur-16-ene:

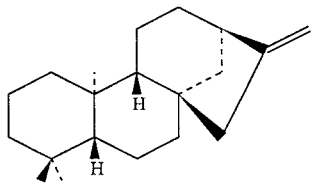

About half of the gibberellins have 20 carbon atoms, and these are referred to as $C_{20}$-gibberellins. The remaining gibberellins lack carbon atom number 20 and are referred to as $C_{19}$-gibberellins. The numbering of the carbon atoms follows the accepted rules for tetracyclic diterpenes (McCrindle and Overton, Advan. Org. Chem. 1965, 5, 47–113) and is used herein (see Formula I). The systematic nomenclature is based on "kaurane" and "gibberellane", and since gibberellins are enantiomers to these compounds, $C_{20}$-gibberellins are termed ent-gibberellanes and $C_{19}$-gibberellins are termed ent-20-norgibberellans. For purposes of expediency, gibberellins are commonly referred to according to a standard numbering system (for example gibberellin $A_1$ or just $GA_1$, and this system will also be employed herein.

In connection with the present invention gibberellins comprise any compound having the ring structure given above.

It is generally accepted that pollen has a general strengthening effect upon human beings as well as a specific effect against chronic inflammation of the prostate (Br. J. Urol. 64 (1989) pp. 496–499); 66 (1990) pp 393–97; 66 (1990) pp 398–404. The positive effect of pollen preparations (such as the Swedish preparations Cernilton and Cernitol) on chronic prostatitis has been scientifically proven, and such preparations are registered as medicaments in certain countries. Pollen is naturally rich in gibberellins, but it has not previously been investigated whether the presence of such gibberellins is involved with pollen's beneficial effects. These pollen preparations are dried water-extracts and their content of gibberellins is 0–1 μg per gram dry material from the extract.

Another natural medicament, Curbicin, is made from an extract of pumpkin seeds and fruits from a dwarf palm, and it is known that pumpkin seeds are also rich in gibberellins, but the effect of gibberellins in this medicament has not been investigated.

Gibberellins have previously been suggested for therapeutic and cosmetic formulations. See for instance WO-A-84/01710; U.S. Pat. Nos. 4,508,707; 4,424,232; and 4,518,614. Biological effects, such as anti-inflammatory effects, in mammals have been described in the scientific literature: Experintia (1977) pp. 1544–45; C. R. Séances Soc. Biol. Filiales 163 (1969) pp. 1302–6; Gen. Physiol. Biophys. 6 (1987) pp. 279–83; Neoplasma (27.2.1980) pp. 203–9; Res. Commun. Chem. Path. Pharm. 28 (1980) pp. 123–32 and J. Am. Pod. Med. Ass. 79 (1989) pp. 24–26. For a review on Pharmacological effects of gibberellinic acid see Pharmazie 38 (1983) pp. 716–8. (It is known that gibberellic acid administered to castrated rats will give restitution of prostate weight; C. R. Séances Soc. Biol. Filiales 163 (1969) pp. 1302–6).

BRIEF DISCLOSURE OF THE INVENTION

It has now been found that gibberellins possess certain important therapeutic properties that previously have been unknown. According to the inventive concept gibberellins will be available for the treatment of prostatitis as given above and/or psoriasis.

Thus one aspect of the invention relates to the use of an active gibberellin for the preparation of a pharmaceutical composition for the treatment of prostatitis (as defined above) and psoriasis. In the preferred mode the gibberellins used comply with the below structure (Formula I).

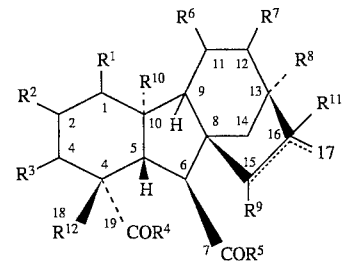

wherein
$R^1$ is H or a group —O—$R^{20}$, where $R^{20}$ is H, or together with $R^2$ or $R^{10}$ forms a bond ($C_1$–$C_2$ or $C_1$–$C_{10}$ double bond, respectively);
$R^2$ is H or a group —O—$R^{21}$, where $R^{21}$ is H, a glycosylic ether group (glycoside ether) or together with $R^4$ forms a bond (lactone) or together with $R^1$ or $R^3$ forms a bond ($C_1$–$C_2$ or $C_2$–$C_3$ double bond, respectively);
$R^3$ is H, =O, or —O—$R^{24}$, where $R^{24}$ is H or a glycosylic ether group (glycoside ether), or together with $R^2$ forms a bond ($C_2$–$C_3$ double bond);
$R^4$ is OH or together with $R^{23}$ or $R^{21}$ forms a bond (lactone);
$R^5$ is H or —O—$R^{22}$, where $R^{22}$ is H or a glycosylic ester (glycoside ester) group;
$R^6$ is H or OH or together with $R^7$ forms a bond ($C_{11}$–$C_{12}$ double bond);
$R^7$ is H, =O, or —O—$R^{25}$, where $R^{25}$ is H or a glycosylic ether group (glycoside ether) or together with $R^6$ forms a bond ($C_{11}$–$C_{12}$ double bond);
$R^8$ is H or —O—$R^{26}$, where $R^{26}$ is H or a glycosylic ether group (glycoside ether), $R^9$ is H or OH;

$R^{10}$ is H, $CH_3$, CHO, COOH or a glycosylic ester (glycoside ester) of said COOH, $CH_2O-R^{23}$ or $-O-R^{23}$, where $R^{23}$ is H or together with $R^4$ forms a bond (lactone), or together with $R_1$ forms a bond ($C_1$–$C_{10}$ double bond);

$R^{11}$ is OH or is absent;

$R^{12}$ is $CH_3$, $CH_2OH$, COOH or an glycosylic ester (glycoside ester) of said COOH;

and pharmaceutical acceptable salts and lactones thereof.

The dotted line together with the solid line indicate that a double bond may be situated between two of the three carbon atoms connected by the dotted and solid lines; with the proviso that a double bond is not present if $R^{11}$ is an OH group.

Formula I complies with normal valence rules, i.e. carbon atoms shall always have four valences, oxygen two and hydrogen one. This leads to the further provisos (i) that $R^1$ and $R^2$ cannot form a bond if $R^{10}$ and $R^1$ and/or $R^2$ and $R^3$ form a bond, and (ii) that $R^{10}$ and $R^1$ cannot form a bond if $R^{10}$ and $R^{23}$ form a bond and (III) that $R^2$ and $R^1$ or $R^2$ and $R^3$ cannot form a bond if $R^4$ and $R^{21}$ form a bond;

For carbon atoms having only three valences in Formal I, the missing valence binds to a hydrogen (not shown).

In a further aspect, the invention relates to a method for treating prostatitis (as given above) and psoriasis, the method comprising administering to a subject suffering from prostatitis an effective amount of an active gibberellin, preferably complying with formula I, or a pharmaceutically acceptable salt or lactone thereof.

With respect to those compounds of formula I which have not previously been used as medicaments, the invention further relates to the use of the compounds as medicaments, in particular for the treatment of prostatitis (as given above) and psoriasis, burns and radiation burns, and for the stimulation of wound healing.

In particular the method relates to the treatment of non-castrated individuals.

The compounds to be used in the invention are active in the sense that they are alleviating the symptoms of prostatitis and psoriasis, respectively. (See "Mechanism of action".)

DETAILED DESCRIPTION OF THE INVENTION

Preferred gibberellins for use in the invention may be divided into six main groups, A–F.

Group A comprises γ-lactonic 12OH gibberellins. The gibberellins of group A comprise compounds of formula I wherein $R^7$ is OH and $R^{10}$ is $-O-R^{23}$, where $R^{23}$ together with $R^4$ forms a bond (lactone). A subgroup of group A is the group in which $R^1$ and $R^2$ together form a bond or $R^2$ and $R^3$ together form a bond. Another subgroup is that in which $R^1$ is H or OH, $R^2$ is H or OH and $R^5$ is $O-R^{22}$. In another subgroup, $R^1$ is H or OH, $R^2$ is H or OH, $R^3$ is H, OH or=0, $R^5$ is OH, $R^6$ is H, $R^8$ is H, $R^9$ is H, $R^{11}$ is absent, and the dotted line together with the solid line indicate that a double bond is situated between two of the three carbon atoms connected by the dotted and solid lines.

Especially preferred compounds of group A are $GA_{30}$, $GA_{31}$, $GA_{33}$, $GA_{48}$, $GA_{49}$, $GA_{58}$, $GA_{69}$, $GA_{70}$ and $GA_{71}$.

Group B comprises γ-lactonic 13-OH gibberellins. The gibberellins of group B comprise compounds of formula I wherein $R^8$ is OH and $R^{10}$ is $-O-R^{23}$, where $R^{23}$ together with $R^4$ forms a bond. One subgroup of group B is that in which $R^1$ and $R^2$ together form a bond, or $R^2$ and $R^3$ together form a bond. In another subgroup, $R^1$ is H or OH, and $R^5$ is $O-R^{22}$. In a further subgroup, $R^1$ is H or OH; $R^2$ is H or a group $-O-R^{21}$, where $R^{21}$ is H, or together with $R^3$ forms a bond ($C_2$–$C_3$ double bond), $R^3$ is H or OH, $R^5$ is OH, $R^6$ is H, $R^7$ is H, $R^{11}$ is absent, and the dotted line together with the solid line indicate that a double bond is situated between two of the three carbon atoms connected by the dotted and solid lines, and either $R^1$ and $R^2$ together may form a bond or $R^2$ and $R^3$ together may form a bond.

Especially preferred compounds of group B are $GA_1$, $GA_3$, $GA_5$, $GA_6$, $GA_8$, $GA_{21}$, $GA_{22}$, $GA_{29}$, $GA_{56}$, $GA_{57}$, $GA_{59}$, $GA_{60}$, $GA_{67}$ and $GA_{72}$.

Group C comprises γ-lactonic 3-oxo gibberellins or gibberellins with or without a hydroxy group in the 3-position. The gibberellins of group C comprise compounds of formula I wherein $R^{10}$ is $-O-R^{23}$, where $R^{23}$ together with $R^4$ forms a bond. In one subgroup of group C, $R^1$ and $R^2$ together form a bond, or $R^2$ and $R^3$ together form a bond (not for 3-oxo gibberellins). In another subgroup, $R^1$ is H or OH, $R^2$ is H or OH, and $R^5$ is $O-R^{22}$. A further subgroup is that in which $R^3$ is H or OH. Still another subgroup is that in which $R^1$ is H or OH, $R^2$ is H or OH, $R^3$ is H or OH, $R^5$ is OH, and $R^{12}$ is $CH_3$.

Especially preferred compounds of group C are 3-oxo gibberellins such as 3-oxo-$GA_1$ and 3-oxo-$GA_3$, and gibberellins with or without a hydroxyl group in the 3-position, such as $GA_1$, $GA_2$, $GA_3$, $GA_4$, $GA_7$, $GA_8$, $GA_9$, $GA_{26}$, $GA_{30}$, $GA_{32}$, $GA_{34}$, $GA_{35}$, $GA_{47}$, $GA_{48}$, $GA_{49}$, $GA_{50}$, $GA_{54}$, $GA_{55}$, $GA_{56}$, $GA_{57}$, $GA_{58}$, $GA_{68}$ and $GA_{71}$.

Group D comprises gibberellin precursors. The gibberellin precursors of group D comprise compounds of formula I wherein $R^7$ is H or OH. A subgroup of group D is that in which $R^1$ is H, $R^2$ is H, and $R^3$ is H or OH. In this subgroup, $R^1$ is H, $R^2$ is H, $R^3$ is H or OH, $R^5$ is H or OH, $R^6$ is H, $R^9$ is H, $R^{10}$ is $CH_3$, CHO or $CH_2O-R^{23}$, where $R^{23}$ together with $R^4$ forms a bond, $R^{11}$ is absent, $R^{12}$ is $CH_3$, and the dotted line together with the solid line indicate that a double bond is situated between two of the three carbon atoms connected by the dotted and solid lines.

Especially preferred compounds of group D are $GA_{12}$-aldehyde, $GA_{12}$, 12α-OH $GA_{12}$-aldehyde, 12α-OH $GA_{12}$, 12α-OH $GA_{14}$, 12α-OH $GA_{15}$, 12α-OH $GA_{37}$, $GA_{19}$ and $GA_{53}$.

Group E comprises various other gibberellins. The gibberellins of group E comprise compounds of formula I wherein $R^{11}$ is absent and $R^{12}$ is $CH_3$. In one subgroup of group E, $R^{10}$ and $R^1$ together form a bond, or $R^1$ and $R^2$ together form a bond, or $R^2$ and $R^3$ together form a bond. In another subgroup, $R^1$ is H, $R^2$ is H and $R^6$ is H. A further subgroup is that in which $R^3$ is H or OH and $R^7$ is H or OH. Still another subgroup is that in which $R^1$ is H, $R^2$ is H, $R^3$ is H or OH, $R^5$ is H or OH, $R^6$ is H, $R^7$ is H or OH, $R^9$ is H, $R^{10}$ is $CH_3$, CHO, $CH_2O-R^{23}$ or $-O-R^{23}$, where $R^{23}$ is H or together with $R^4$ forms a bond, and the dotted line together with the solid line indicate that a double bond is situated between two of the three carbon atoms connected by the dotted and solid lines.

Group E comprises gibberellins such as $GA_1$, $GA_3$, $GA_4$, $GA_7$, $GA_9$, $GA_{12}$, $GA_{12}$-aldehyde, $GA_{14}$, $GA_{14}$-aldehyde, $GA_{15}$, $GA_{18}$, $GA_{18}$-aldehyde, $GA_{19}$, $GA_{20}$, $GA_{23}$, $GA_{24}$, $GA_{30}$, $GA_{36}$, $GA_{37}$, $GA_{38}$, $GA_{44}$ and $GA_{53}$-aldehyde.

Group F comprises gibberellin conjugates such as gibberelin ethers and esters. Examples of ethers are glycosylic ethers (glycoside ethers) wherein the preferred glycoside bond is a O-β-D-glycoside bond and the sugar component is selected from the group consisting of glucose, galactose, arabinose and xylose. In general, ether gibberellin conjugates are formed at the $R^{21}$, $R^{24}$, $R^{25}$ and/or $R^{26}$ position of formula I, although it may also occur at other positions. One or more of these positions may be transformed into an ether group. Especially preferred gibberellin ethers are $GA_1$-3-O-β-D-glucoside, $GA_1$-13-O-β-D-glucoside, $GA_3$-3-O-β-D-glucoside, $GA_3$-13-O-β-D-glucoside, $GA_3$-3,13-di-O-β-D-glucoside, $GA_4$-3-O-β-D-glucoside, $GA_7$-3-O-β-D-glucoside, $GA_{19}$-13-O-β-D-glucoside, $GA_{20}$-13-O-β-D-glucoside, $GA_{30}$-12-O-β-D-glucoside and $GA_{53}$-13-O-β-D-glucoside. Preferred esters are glycosylic esters (glycoside esters) wherein the sugar is an α-D, an α-L, a β-D or a β-L sugar. In general, the ester is formed at the $R^{22}$ position of formula I, but the ester can be formed at any position which has a carboxylic acid functional group, e.g. at positions $R^{10}$ or $R^{12}$, respectively, when the $R^{10}$ and/or $R^{12}$ group is a COOH group. The alcoholic part of the ester is typically a sugar residue, especially a sugar residue selected from the group consisting of glucose, galactose, arabinose and xylose (all of which being in form of glycosidyl groups). Preferred compounds are those wherein the ester bond formed in the $R^{22}$ position is selected from the group consisting of a β-D-glucosidyl, an α-D-glucosidyl, a β-D-galactosidyl, an α-L-arabinosidyl and a β-D-xylosidyl ester bond. The preferred gibberellin esters are α- and β-glycoside esters, such as $GA_1$-D-glucosyl ester, $GA_3$-D-glucosyl ester, $GA_4$-D-glucosyl ester, $GA_7$-D-glucosyl ester, $GA_9$-D-glucosyl ester, $GA_{19}$-D-glucosyl ester, $GA_{20}$-D-glucosyl ester, $GA_{30}$-D-glucosyl ester and $GA_{53}$-D-glucosyl ester ring structure wherein the carbohydrate moiety may be bound to the gibberellin ring structure in the positions given above.

A number of the naturally occurring gibberellins are commercially available. Gibberellins which are not marketed may be prepared by chemical synthesis e.g. using commercially available gibberellins as starting materials or by synthesis by fungi. The synthesis may, if necessary, be followed by conversion of the isolated compounds into the desired gibberellins.

Chemical synthesis of gibberellin precursors and gibberellins

Total synthesis of gibberellin precursors and gibberellins is very complicated, time consuming and very expensive. The yields are usually also very low. Therefore, if possible, the method of choice is to use fungal cultures which are specially designed to synthesize specific gibberellin precursors, gibberellins and gibberellin conjugates. If this is not feasible, methods for total synthesis described in the literature (Mori et al., 1969, Tetrahedon 25: 1293; Nagata et al., 1971, J. Am. Chem. Soc. 93: 5740; Corey et al., 1978, J. Am. Chem. Soc. 100: 8034; Mander, 1982, Search 13: 188) may be employed. A simple way of producing $GA_1$, 3-oxo-$GA_1$, 3-oxo-$GA_3$, $GA_4$, $GA_5$, and $GA_{20}$ is to use the commercially available $GA_3$ as a starting material. The preparations of these gibberellins from $GA_3$ is described in Example 4. Other desired gibberellins may similarly be prepared by using appropriate gibberellins as starting materials.

Synthesis by fungi

Although chemical synthesis is a possibility, the best method of large-scale production of gibberellins is probably synthesis by fungi, optionally followed by conversion of the isolated compounds to other gibberellin compounds. The naturally occurring gibberellin-producing fungi (especially *Gibberella fujikuroi*; also the genus Sphacaeoloma) primarily produce $GA_3$, $GA_4$ and $GA_7$. Other gibberellins may be produced by mutated fungal strains. Mutation has especially been achieved by UV treatment, but other methods of mutation, for example chemical treatment, may also be employed. Identification of the mutated strains is especially performed by immunoassay techniques, using gibberellin antibodies.

Pharmaceutical compositions

The formulations used in connection with therapeutically active gibberellins are designed to be administered orally or parenterally in dosage forms containing conventional, nontoxic pharmaceutically acceptable carriers and excipients.

Formulations for oral use include tablets, e.g. effervescent tablets or chewable tablets, lozenges, capsules, powders, granules, mixtures, syrups, solutions, suspensions, emulsions, and the like.

The solid dosage forms (e.g. tablets, capsules, granules etc.) may comprise the active ingredient in admixture with nontoxic pharmaceutically acceptable carriers and/or excipients. These include binding agents such as starch, gelatin, acacia or polyvinylpyrrolidone; fillers such as lactose, microcrystalline cellulose, potato starch, maize starch, calcium phosphate, calcium carbonate, sodium chloride, sugar or sorbitol; granulating agents or disintegrants such as potato starch or alginic acid; wetting agents such as sodium lauryl sulphate; and lubricants such as magnesium stearate, talc, stearic acid, polyethylene glycol or silica.

Liquid preparations for oral administration (e.g. mixtures, syrups, solutions, suspensions, emulsions etc.) may comprise the active ingredient in admixture with suitable pharmaceutically acceptable additives such as suspending agents, e.g. gelatin, methyl cellulose, hydroxyethyl cellulose, sodium carboxymethyl cellulose, hydroxypropyl cellulose, sodium alginate, polyvinylpyrrolidone, gum tragacanth and gum acacia; emulsifying agents, e.g. lecithin and sorbitan monooleate; dispersing or wetting agents, e.g. lecithin and polyoxyethylene esters (e.g. polyoxyethylene stearate); non-aqueous vehicles, e.g. vegetable oils (arachic oil, olive oil, almond oil, sesame oil, coconut oil) and mineral oils (paraffin); preservatives, e.g. methyl, ethyl or n-propyl p-benzoates; and one or more colouring agents, flavouring agents and/or sweetening agents, e.g. sucrose or saccharin.

The tablet formulations may be uncoated or they may be provided with a coating by known techniques to control the release of the active substance or to delay disintegration and absorption in the gastrointestinal tract.

Formulations for parenteral use include injectable, infusable and implantable compositions. Potential administration routes are the intravenous, intramuscular, or subcutaneous route. Formulations for injection may be presented in unit dose form, e.g. ampoules, or in multi-dose containers with an added preservative. The compositions may be in form of a solution, a suspension or an emulsion or may be presented as a dry powder to be reconstituted with water or another suitable vehicle before use. The compositions comprise the active ingredient in admixture with suitable pharmaceutically acceptable carriers and/or excipients. The composition may additionally comprise formulatory agents such as suspending stabilising and/or dispersing agents.

The oral and parenteral route of administration is especially preferred for the treatment of prostatitis as defined above.

Furthermore, the gibberellins as given above may be administered topically to the skin in dosage forms or compositions comprising the active ingredient in admixture with nontoxic pharmaceutically acceptable carriers and/or excipients. Formulations for topical use include creams, ointments, lotions, liniments, gels, hydrogels, solutions, suspensions, emulsions, pastes, plasters and other kinds of transdermal delivery systems. Pharmaceutically acceptable carriers or excipients are for example ointment bases (e.g. paraffin, vegetable oils, polyethylene glycols, Span $^{(R)}$ and Tween[R]; suspending agents; emulsifying agents (e.g. lecithin, gum acacia and sorbitan monooleate derivatives); gel-forming agents (e.g. Carbopol, alginates, gelatin and cellulose derivatives); antioxidants (e.g. ascorbic acid, tocopherol and derivatives thereof and butylated hydroxy anisol); buffering agents; preservatives (e.g. benzalkonium chloride and parabens); humectants (e.g. glycerin, propylene glycol and urea); penetration enhancers (e.g. propylene glycol, DMSO, Azone[R], and triethanolamine); and perfumes and skin protective agents.

Administration of the gibberellin of the present invention by the topical route is especially preferred for the treatment of psoriasis, burns and radiation burns and for the stimulation of wound healing.

The formulation of the above-mentioned compositions will be well known to those skilled in the art of pharmaceutical formulation. Specific outlines for formulating the composition can be found in "Remington's Pharmaceutical Sciences" (16th. Ed. (1980), Mack Publishing Company, Easton, U.S.A.).

Dosage

The therapeutic dosage range for therapeutically active gibberellins will depend on a number of factors such as the patient's age and weight and the particular condition being treated and the specific gibberellin selected.

A unit dosage form, such as a tablet or a capsule, normally comprise about 10 µg–5 mg of the active compound of the invention, in particular about 100–500 µg. The daily dosage as employed for treatment of a human adult weighing approximately 70 kg will preferably range from about 50 to about 1000 µg per day, most preferably from about 100 to 500 µg per day and may be administered in about 1–3 doses per day depending on the route of administration and on the condition being treated.

An effective dose for treating prostatitis, in particular for inhibiting and decreasing hypertrophy and hyperplastic adenoma in the prostate of male humans is about 100–500 µg of the gibberellins, gibberellin precursors or gibberellin conjugates per day for a period of three weeks. The most effective gibberellins for the treatment of hypertrophy and hyperplastic adenoma in the prostate are -lactonic C-19 gibberellins hydroxylated in positon 12, e.g. $GA_{30}$, $GA_{31}$, $GA_{33}$, $GA_{48}$, $GA_{49}$, $GA_{58}$, $GA_{69}$, $GA_{70}$, $GA_{71}$. Other therapeutically active gibberellins are -lactonic C-19 gibberellins hydroxylated in position 13, e.g. $GA_1$, $GA_3$, $GA_5$, $GA_6$, $GA_8$, $GA_{21}$, $GA_{22}$, $GA_{29}$, $GA_{56}$, $GA_{57}$, $GA_{59}$, $GA_{60}$, $GA_{67}$, $GA_{72}$ and -lactonic C-19 gibberellins with no hydroxyl group or with a hydroxyl group in position 3, e.g. $GA_1$, $GA_2$, $GA_3$, $GA_4$, $GA_7$, $GA_8$, $GA_9$, $GA_{26}$, $GA_{30}$, $GA_{32}$ $GA_{34}$, $GA_{35}$, $GA_{47}$, $GA_{48}$, $GA_{49}$, $GA_{50}$, $GA_{54}$, $GA_{55}$, $GA_{56}$, $GA_{57}$, $GA_{58}$, $GA_{68}$, $GA_{71}$. In addition, preparations containing gibberellins and gibberellin precursors such as $GA_{12}$-aldehyde, $GA_{12}$, 12α-OH $GA_{12}$-aldehyde, 12α-OH $GA_{12}$, 12α-OH $GA_{14}$, 12α-OH $GA_{15}$, 12α-OH $GA_{37}$, $GA_{53}$ and $GA_{19}$ are therapeutically active.

The pharmaceutical composition according to the invention may be administered in combination with other therapeutic agents.

In case the gibberellin used originates from extraction of pollen the composition of the invention contains more than 10 µg gibberellin per gram of dry matter in the extract.

The best modes of the invention known at the priority date are represented by examples 5 and 6.

Mechanism of action

While not wishing to be bound by any particular theory, it is believed that the gibberellins function as described in the following.

The action of the gibberellins, gibberellin precursors and gibberellin conjugates is believed to depend mainly on their steroid-like action. Although not being structurally steroid-like, their physiological action is believed to be steroid-like. The activity of the gibberellin conjugates depends on a hydrolysis to free gibberellins. The hydrolysis is either caused by enzymatic cleavage by e.g. glucosidase or by extreme pH-values. The following model is proposed to explain the action of gibberellins and gibberellin precursors on prostatitis. The model also gives an explanation of the anabolic and libido-increasing effect of the gibberellins and gibberellin precursors.

The gibberellins and gibberellin precursors have a structural similarity with testosterone and therefore bind to the testosterone receptors. The gibberellin or gibberellin precursor receptor-complex is functionally similar to the testosterone and testosterone receptor-complex. The physiological effects exerted by testosterone are therefore mimicked by the gibberellins and gibberellin precursors. The effect on hyperplasia or hypertrophic growth of the prostatic glands is also a result of the testosterone-like activity. In this case, the gibberellins or gibberellin precursors are thought to bind to the enzyme 5-α reductase, which normally converts testosterone to dihydrotestosterone. Dihydrotestosterone is normally synthesized from testosterone in the prostate, as well as in other target tissues, and causes enlargement of the prostate. If the concentration of gibberellins or gibberellin precursors in the prostate is high enough, the 5-α reductase can be blocked by the gibberellins or the gibberellin precursors. This causes a decrease in the amount of dihydrotestosterone and subsequently also a decreased enlargement of the prostate.

The gibberellins and the gibberellin precursors are also clearly antiphlogistic in their action. A decreased swelling of the prostate as soon as four hours after administration of 1 mg of gibberellin $GA_4$ was observed by rectal palpation on a male patient suffering from hyperplastic adenoma of the prostate. The antiphlogistic effect is probably due to a glucocorticoid-like action of the gibberellins or gibberellin precursors. The decreased local inflammation in the prostate is thought to be partly due to inhibition of phospholipase by $GA_4$, which results in a lower release of arachidonic acid from phospholipids. This in turn will result in a decreased formation of leucotrienes, thromboxanes, prostaglandins and prostacyclin. The gibberellins or gibberellin precursors are also thought to stabilize lysosomal membranes and inhibit lysosomic enzymes, resulting in an increased stability of lysosomes.

Another very important action of gibberellins and gibberellin precursors is that they increase the activity of adenylate and guaylate cyclase. The intracellular concentration of cyclic AMP and cyclic GMP may therefore be increased by administration of gibberellins and gibberellin precursors. The rise in cyclic AMP and cyclic GMP then results in an inhibition of a wide range of proinflammatory functions, such as lymphocyte stimulation and the release of inflammatory mediators such as histamine and lysosomal enzymes. The increase in cyclic-GMP and cyclic-AMP also results in a normalization of cell divisions and cell proliferation in the epidermal cells.

The action of gibberellins, gibberellin precursors and gibberellin conjugates has also proved to have an immuno-activating character, since the amounts of non-specific antibodies increase after administration.

The invention will be further illustrated by the following non-limiting examples.

EXAMPLE 1

Isolation of gibberellin precursors, gibberellins and gibberellin-conjugates from pollen of different species, pumpkin (*Cucurbita maxima* L.) seeds, fruits from *Sabal serrulata* (Münch.) Benth. et Hook and the parenchymateous gel of *Aloe barbadensis* Mill.

a) Extraction and purification of gibberellin precursors, gibberellins and their conjugates Pollen from various plant species (*Secale cereale, Zea mays, Alnus incana, Pinus sylvestris, Picea abies*) seeds from *Cucurbita maxima*, gel from *Aloe barbadensis* or fruit from *Sabal serrulata* was homogenized in 10 ml of ethanol (EtOH) per g (fresh weight) of plant material. The sample was extracted in the dark at 4° C. with continuous stirring for 2 h. After filtering through a Whatman OOH filter, the tissue debris was washed with 200 ml of fresh EtOH. Ten ml of 0.5M sodium phosphate buffer, pH 8.0, was added to the pooled EtOH, and the EtOH was evaporated to dryness under reduced pressure at 40° C. The aqueous residue was adjusted to a volume of about 10 ml with water and the pH was adjusted to 8.0 with NaOH or HCl. The extract was applied to a 300×20 mm internal diameter (i.d.) column which was packed with insoluble poly-N-vinylpolypyrrolidone, and was eluted with 0.1M sodium phosphate buffer, pH 0.8. The 0–200 ml fraction was collected, acidified to pH 2.7 with 6M HCl and extracted 5 times with 100 ml of ethyl acetate (EtOAc). After extraction with EtOAc, the buffer phase was extracted 5 times with 100 ml of water-saturated n-butanol (n-BuOH). The acidic EtOAc extracts containing the free gibberellins were combined and the water was removed by freezing and filtering. The EtOAc was evaporated to dryness under reduced pressure at 40° C. The acidic n-butanol fractions containing the conjugated gibberellins were combined and the solvent was evaporated to dryness under reduced pressure at 70° C.

b) High performance liquid chromatography (HPLC)

The acidic EtOAc extracts and the acidic n-BuOH extracts were further purified using a reverse phase HPLC system consisting of two Waters M501 pumps (Millipore AB, Västra Frölunda, Sweden) connected to a 10 mm (i.d.)×250 mm steel column packed with 5 µm Polygosil $C_{18}$ (Skandinaviska Genetec AB, Kungsbacka, Sweden). The pumps were controlled by a Waters M680 system controller and the injector was a Waters U6K. The mobile phase consisted of a linear gradient from water and acetic acid (99.1, v/v) to methanol (MeOH) and acetic acid (99:1, v/v). The gradient sweep time was 60 min and the flow rate was 1 ml min$^{-1}$. Sixty 1 ml fractions were collected and evaporated in a Savant Speed Vac Concentrator (Tectum Instruments, Umeå, Sweden). Each of these fractions were dissolved in 50 µl of 95% ethanol and tested in ¹⁄₁₀₀ aliquots for GA-like activity with the Tan-ginbozu dwarf rice microdrop bioassay (Murakami, 1968, Bot. Mag. 81: 33), which was modified by the use of 0.5 µl microdrops.

The remaining part of the fractions exhibiting biological activity was further purified by analytical normal phase HPLC. This system consisted of the same Waters equipment as described above with a 150 mm×4.6 mm (i.d.) column packed with 5 µm of Nucleosil $NO_2$ (Skandinaviska Genetec AB, Kungsbacka, Sweden) forming the stationary phase. The mobile phase was a linear gradient from n-heptane half-saturated with 0.5M formic acid in water to EtOAc-water-formic acid (98.5:1:0.5, v/v). The gradient sweep time was 60 min and the flow rate was 2 ml min$^{-1}$. Sixty 2 ml fractions were collected and evaporated in the Speed Vac concentrator, and the GA-like activity was tested using the Tan-ginbozu dwarf rice bioassay (Murakami, 1968). The identity of the different gibberellins which were detected was elucidated by gas chromatography and mass spectrometry as described below.

c) Gas chromatography and mass spectrometry

Samples intended for analyses by gas chromatography and mass spectrometry were methylated with ethereal diazomethane. After evaporation, 50 µl of N,O-bis(trimethylsilyl)trifluoroacetamide with 1% trimethylchlorosilane was added to each sample, and the mixtures were heated to 90° C. for 30 min. After evaporation, the methylated and trimethylsilylated samples were dissolved in heptane and injected splitless into a fused silica capillary column, SE-30 chemical bonded phase, 25 m long, 0.25 mm i.d. and 0.25 µm film thickness (Quadrex Co., U.S.A.) connected to a Hewlett Packard 5970B Mass Selective Detector and a Hewlett Packard 59970B Workstation (Hewlett Packard, Spånga, Sweden). If the compound was suspected to be a methylester only, the solvent was methanol. The injection temperature was 230° C. The column temperature was maintained at 60° C. for 1 min, then was increased by 20° C. min$^{-1}$ up to 200° C. followed by an increase of 4° C. min$^{-1}$ to 250° C. The column effluent was led into the ion source with an interface temperature of 275° C. The electron energy was 70 eV. Electron impact spectra of the extract fractions were recorded and compared with spectra of standards. The samples and standards were also co-injected with n-alkanes $C_{23}$–$C_{28}$ (Gaskin et al., 1971, Phytochemistry 10: 1155). A linear regression was made between the retention time and the number of carbons. Kovats retention indices (Kovats, 1959, Helv. Chim. Acta 41: 1915) were calculated by converting the retention times to number of carbons and finally multiplying this by 100.

d) Crystallization

The gibberellin precursors, gibberellins and gibberellin conjugates purified in the above manner were dissolved in a small amount of cyclohexane, crystallized at −20° C. and used in therapeutic tests as described below. In this manner, $GA_1$, $GA_3$, $GA_9$, $GA_{19}$, $GA_{20}$ and $GA_{53}$ were obtained from the pollen preparations, $GA_{30}$ from the pumpkin seed (*Cucurbita maxima* L.), $GA_3$ and $GA_7$ from the Aloe gel and $GA_{12}$-aldehyde from the dwarf palm (*Sabal serrulata*).

Comments to ethanol extraction

Extraction of pollen in ethanol results in a high yield of physiologically active gibberellins. Ethanol extraction is also advantageous since compounds of higher molecular weights, like proteins, complex carbohydrates and amino-sugars are not efficiently extracted. Since the extract is also filtrated through a 45 µm 'filter and a 10,000 Dalton filter, the molecular sizes of the compounds in the extract are limited. This makes the extract less allergenic and also more concentrated with active compounds, gibberellins, as compared with extraction in aqueous media. The dry matter content after ethanol extraction of pollen is ca. 10% as compared with a dry matter content of ca. 30–50% in the case of water extraction. The degradation of gibberellins by enzymatic processes in aqueous media can be highly-significant. This degradation is reduced when ethanol is used as solvent since the enzymes are precipitated. For these reasons an ethanol extract will, when properly prepared, contain 10–100 times more active compounds, gibberellins, per mass unit extract, i.e. the dry matter of an ethanol extract will contain 10 µg/g or more, normally 10–1000 µg/g. An optimized handling of the pollen prior to extraction may additionally increase the concentration of active compounds in the final extract.

EXAMPLE 2

Synthesis of gibberellins by the fungi *Gibberella fujikuroi* (Saw.) Woll or the asexual form *Fusarium moniliforme* (Sheld.) Winel.

Gibberellin precursors, gibberellins and their conjugates were produced by the cultivation of the fungus *Gibberella fujikuroi* (Saw.) Woll or the asexual form *Fusarium moniliforme* (Sheld.) Winel, both of which are isolated from soil. Different strains of the fungus selected for a high production of gibberellin precursors, gibberellins and their conjugates were maintained at 4° C. on a medium containing 20 g agar, 5 g glucose, 100 ml of potato juice and 900 ml of water. The medium was autoclaved and the fungus was inoculated and grown for 10–14 days at 28° C. The fungus can then be stored at 4° C. for about 2 months. The gibberellin production was started by inoculating the fungus into a preculture medium containing 200 g sucrose, 15 g diammoniumhydrogencitrate, 1 g $Ca(NO_3)_2$, 4 $H_2O$, 0.25 g $KH_2PO_4$, 0.3 g $MgSO_4$, 7 $H_2O$, 0.01 g $FeSO_4$, 7 $H_2O$, 0.03 g $ZnSO_4$, 7 $H_2O$, 0.1 g KCl and 1000 ml distilled water. The medium was autoclaved before use. One gram of the fungus taken from the storage medium was inoculated and grown in 100 ml of the preculture medium at 28° C. for 3–4 days. The mycelia was then filtered off, washed with distilled water and gently mechanically broken into smaller pieces with a mortar and pestle. The fungus was then inoculated into a medium consisting of 50 g glucose, 1.2 g $NH_4NO_3$, 5 g $KH_2PO_4$, 1 g $MgSO_4$, 7 $H_2O$ and 2 ml of a trace element solution consisting of 1 g $FeSO_4$, 7 $H_2O$, 88 mg $Na_2B_4O_7$, 10 $H_2O$, 392 mg $CuSO_4$, 5 $H_2O$, 72 mg $MnCl_2$, $H_2O$, 37 mg $(NH_4)_6Mo_7O_{24}$, 4 $H_2O$ and 2.2 mg $ZnSO_4$, 7 $H_2O$ per 1000 ml of distilled water. The mix was adjusted to a volume of 1000 ml with distilled water and adjusted to a pH of 4.5 with HCl or NaOH. The fungus was grown on a shaker for 10 days at 28° C. The gibberellin precursors, gibberellins and their conjugates were then isolated from the medium by the procedure described in Example 1.

EXAMPLE 3

Mutation and selection of highly gibberellin-productive strains of *Gibberella fujikuroi* (Saw.) Woll.

Strains high in production of gibberellins $GA_1$, $GA_3$, $GA_4$, $GA_9$, $GA_7$ and $GA_{20}$ were isolated, after mutation of fungal protoplasts with N-methyl-N'-nitro-N-nitrosoguanidin (NTG), by screening with gibberellin-specific antibodies.
Protoplast production Fungal mycelium was isolated from a preculture medium (see Example 2) by filtration and incubated in 10 ml of a lytic enzyme preparation consisting of 20 µg per ml of Cellulase "Onozuka R-10" (tricoderma viride) 1.3 U/mg (Serva, West Germany, EC 3.2.1.4) and 5 µg per ml Driselase 26.5 U/mg (Fluka, Switzerland). The enzymes were dissolved in a 0.7M solution of $MgSO_4$ as an osmotic stabilizer and the mycelium was treated for 4 hours at 32° C. with reciprocal shaking.

After incubation, the protoplast solution was filtered through glass wool and centrifuged at 500× g for 10 minutes. The protoplast pellet was then washed with 10 ml of 0.7M $MgSO_4$ and centrifuged at 500× g for 10 minutes. The pellet was then suspended in 10 ml of 0.7M $MgSO_4$ solution containing 0.1 mg of N-methyl-N'-nitro-N-nitrosoguanidin (NTG, Aldrich, West Germany).

After incubation for one hour at room temperature, the protoplasts were centrifuged at 500× g for 10 minutes. The supernatant was discarded and the pellet was washed with 10 ml 0.7M $MgSO_4$ and centrifuged at 500× g for 10 minutes. The washing procedure was repeated five times. The protoplasts were diluted and plated on a solid medium containing 2 g agar, 0.5 g glucose and 10 ml of potato juice per 100 ml of water. 0.7M mannitol was added to the medium as an osmotic stabilizer. The plates were incubated at 28° C. for 7 days and regenerated protoplasts were isolated and suspended in 0.2 ml of a production medium consisting of 50 g glucose, 1.2 g $NH_4NO_3$, 5 g $KH_2PO_4$, 1 g $MgSO_4$, 7 $H_2O$ and 2 ml of the trace element solution of Example 2. The mix was adjusted to a volume of 1000 ml with distilled water and adjusted to pH 4.5. The fungus was grown in the wells of a microtiter plate for 7 days at 28° C. The medium was thereafter tested for gibberellin-binding activity in radioimmunoassays using antibodies against $GA_1$, $GA_3$, $GA_4$, $GA_7$, $GA_9$ and $GA_{20}$.
Radioimmunoassays Conjugation of $GA_1$, $GA_3$, $GA_4$, $GA_7$, $GA_9$ and $GA_{20}$ to bovine serum albumin was made according to Weiler and Wieczorek (1981, Planta 152:159). Rabbit immunizations and antiserum production were made by Dakopatts, Copenhagen, Denmark. The binding properties of these polyclonal antibodies were tested before use. Samples and standards were methylated with ethereal diazomethane before the radioimmunoassay (RIA). The assay mixtures consisted of 300 µl of saline phosphate buffer (PBS) pH 8.0 (0.01M phosphate and 0.15M NaCl) plus 100 µl of methylated standard ($GA_1$, $GA_4$ or $GA_{20}$), methylated samples or methylated blank samples in PBS buffer plus about 100 Bq methylated tracer in 100 µl PBS buffer ([1,2-$^3$H]$GA_{20}$, 1,1 TBq/mmol, [1,2-$^3$H]$GA_4$, 37 GBq/mmol, [2,3-$^3$H]$GA_9$, 1.7 TBq/mmol, [1,2-$^3$H]$GA_{20}$, 1,1 TBq/mmol) plus 100 µl serum. The non-specific binding was determined by excluding the serum. The contents of the vials were mixed and incubated for 2 h. 0.6 ml of a saturated ammonium sulphate solution was added to the vials and after centrifugation for 0.5 h at 2000× g, the supernatants were discarded, the pellets were dispersed in 100 µl of water, 1 ml of Miniria 20 liquid scintillater was added, and radioactivity was determined by liquid scintillation spectrometry. The antibody binding activity of the extract fractions was calculated using the formula $(B-N)/(B_0-N)\times 100$, where B is the tracer binding in the presence of standard or samples, $B_0$ is the tracer binding in the absence of standard or sample and N is the non-specific binding.

Colonies producing substances inhibitory to the binding in either of the radioimmunoassays were isolated and grown in a larger volume of pre-culture medium, transferred to production medium, and the gibberellins were extracted and isolated as described in Example 1. The gibberellins were separated by HPLC and identified by gas chromatography and mass spectrometry.

EXAMPLE 4

Chemical synthesis of gibberellins

The commercially available gibberellin $GA_3$ may be used as the starting material for the production of $GA_1$, 3-oxo-$GA_1$, 3-oxo-$GA_3$, $GA_4$, $GA_5$ and $GA_{20}$. $GA_3$ was first methylated with diazomethan in ether (Schlenk and Gellerman, 1960, Analytical Chemistry 32: 1412). The 1,2 double bond in $GA_3$-Me was then hydrogenated with 2% palladium barium carbonate in ethyl acetate and pyridine (Jones and McCloskey, 1963, J. Appl. Chem. 13: 324) yielding $GA_1$-Me. The methyl ester bond was then hydrolyzed in 0.5M potassium hydroxid at 70° C. for two hours, yielding $GA_1$. The 3β-hydroxy group of $GA_3$-Me may also be oxidized with barium manganate in methylene chloride for two days. This yields 3-oxo-$GA_3$-Me, which can be further hydrogenated to 3-oxo-$GA_1$ with 2% palladium barium carbonate in ethyl acetate and pyridine (Jones and McCloskey, 1963). The methyl ester bond was then hydrolyzed in 0.5M potassium hydroxide at 70° C. for two hours, yielding 3-oxo-$GA_3$ and 3-oxo-$GA_1$. The $GA_1$-Me can also be converted to $GA_5$-Me by first preparing 3-tosyl-$GA_1$-Me by dissolving the $GA_1$-Me in pyridine and adding 6% (w/v) of tosyl chloride. The reaction products were isolated after 10 days and separated by HPLC. The $GA_5$-Me was converted to free acid by hydrolysis in 0.5M potassium hydroxide at 70° C. for two hours. $GA_5$-Me was also converted to $GA_{20}$-Me by hydrogenation over 2% palladium barium carbonate. The $GA_{20}$-Me may then be converted to free acid by hydrolysis in 0.5M potassium hydroxide at 70° C. for two hours.

EXAMPLE 5

Treatment of prostatitis, hypertrophy and hyperplastic adenoma in the prostate with gibberellins $GA_{20}$ and $GA_{30}$ Pharmaceutical compositions were prepared by dissolving 50 mg each of gibberellins $GA_{20}$ and $GA_{30}$ in 1 ml of 95% ethanol and diluting this solution prior to use to a volume of 10 ml with water. The gibberellins were then added to rat food and fed to rats in amounts of 100 µl, 20 µl, 10 µl and 2 µl. This dosage was administered daily for three months to male Wistar rats (three rats per dose).

RESULTS

Treatment of the male Witstar rats with 50 µg each of gibberellin $GA_{20}$ and $GA_{30}$ for a period of three months resulted in a significant increase in body weight of 19% compared to control animals. Animals treated for three months with gibberellins $GA_{20}$ and $GA_{30}$ had a mean weight of 296 grams compared with 249 grams for control animals. The weight of the prostate in relation to the total body weight was significantly smaller in animals treated with the gibberellins in the manner described above. The weight of the prostate in percent of the total body weight was 0.27% (672 mg) for control animals and 0.18% (562 mg) for animals treated with the gibberellins. When rats castrated as young animals were treated in the same manner, a similar response was obtained.

The gibberellins also exert a significant anabolic and myotrophic effect on castrated rats. The treatment of castrated rats with the gibberellins resulted in an increase of 9% in body weight as compared with untreated castrated animals. The weight of the prostate was also significantly increased by the treatment with the gibberellins. A mean prostate weight of 80 mg was obtained in untreated animals, while a mean prostate weight of 350 mg was obtained in castrated rats treated with the gibberellins. This corresponds to a prostate weight of 0.04% in relation to the total body weight for untreated castrated rats and a prostate weight of 0.14% in relation to the total body weight for treated castrated rats.

Experimentally induced hypertrophic growth of the prostatic gland in rats by dihydrotestosterone was also inhibited by the gibberellins. Treatment of male adult uncastrated rats with a daily 50 µg doses of dihydrotestosterone for three months resulted in hypertrophic growth of the prostate gland. The weight of the prostate was 814 mg, which was equivalent to about 0.34% of the total body weight. When the rats were simultaneously given a daily dose of 100 µg of gibberellins $GA_{20}$ and $GA_{30}$, an increase in prostate weight was not detected. The weight of the prostate was in this case 582 mg, which was equivalent to 0.20% of the total body weight.

Hyperplasia and hypertrophic growth of the prostate glands in male humans was also reduced by treatment with gibberellins $GA_{20}$ and $GA_{30}$. The substances were administered orally in a weak ethanol solution containing doses of 10 µg, 50 µg, 100 µg, 500 µg and 1 mg per day for three weeks. The treatment resulted in a reduced swelling and a reduced growth of the prostate. The treatment with the gibberellins also resulted in a slight increase in body weight and a slight increase in libido.

EXAMPLE 6

The use of gibberellin $GA_7$ for the treatment of psoriasis

Pharmaceutical compositions for topical applications were made by dissolving gibberellin $GA_7$ in ethanol and subsequently adding this solution to a cream consisting of medical vaseline with 0.05% ascorbic acid. The cream contained gibberellin $GA_7$ in a concentration of either 0.1 mg/g, 0.5 mg/g, 1 mg/g, 5 mg/g or 10 mg/g. The cream was topically applied on the psoriatic rash of a female patient twice a day for a period of three weeks. One weeks use resulted in a significant decrease in the degree of the psoriatic rash.

I claim:

1. A method for decreasing prostate mass comprising administering an effective amount of a gibberellin compound of the formula:

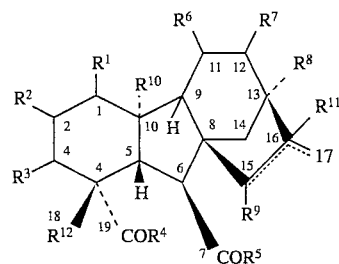

wherein $R^1$ is selected from the group consisting of H and a group —O—$R^{20}$, wherein $R^{20}$ is H, or together with $R^2$ or $R^{10}$ forms a double bond;

$R^2$ is selected from the group consisting of H and a group —O—$R^{21}$, wherein $R^{21}$ is selected from the group consisting of H, and a glycoside group, or together with $R^4$ forms a lactone ring or together with $R^1$ or $R^3$ forms a double bond;

$R^3$ is selected from the group consisting of H, =O and —O—$R^{24}$, where $R^{24}$ is selected from the group consisting of H and a glycoside group, or together with $R^2$ forms a double bond;

$R^4$ is OH or together with $R^{23}$ or $R^{21}$ forms a lactone ring;

$R^5$ is H or —O—$R^{22}$, where $R^{22}$ is H or a glycoside group;

$R^6$ is H, OH or together with $R^7$ forms a double bond;

$R^7$ is selected from the group consisting of H, =O, or —O—$R^{25}$, where $R^{25}$ is H, a glycoside group or together with $R^6$ forms a double bond;

$R^8$ is H or —O—$R^{26}$, where $R^{26}$ is H or a glycoside;

$R^9$ is H or OH;

$R^{10}$ is selected from the group consisting of H, $CH_3$, CHO, COOH and a glycoside ester of said COOH, $CH_2O$—$R^{23}$ or —O—$R^{23}$, where $R^{23}$ is H or together with $R^4$ forms a lactone ring or together with $R^1$ forms a double bond;

$R^{11}$ is OH or is absent, with the proviso that the dotted line together with the solid line represent that there is a double bond between two of the three carbons connected by the dotted line when $R^{11}$ is absent;

$R^{12}$ is selected from the group consisting of $CH_3$, $CH_2OH$, COOH and a glycoside ester of said COOH;

and pharmaceutically acceptable salts and lactones thereof, to a mammal in need of such treatment.

2. The method of claim 1, wherein at the most four of $R^1$, $R^2$, $R^3$, $R^6$, $R^7$, $R^8$, $R^9$ and $R^{11}$ are OH.

3. The method according to claim 1, wherein
   (i) one or more of $R^{21}$, $R^{24}$, $R^{25}$ and $R^{26}$ are selected from the group consisting of glucose, galactose, arabinose and xylose, all of which being bound glycosidically to the oxygen atom in $OR^{21}$, $OR^{24}$, $OR^{25}$ or $OR^{26}$; or
   (ii) at least one of $R^{10}$, $R^{12}$ and $COR^5$ is an ester group in which the alcohol moiety is a glycosidic group.

4. The method according to claim 1, wherein
   (i) one or more of $R^{21}$, $R^{24}$, $R^{25}$ and $R^{26}$ are selected from the group consisting of glucose, galactose, arabinose and xylose, all of which being bound glycosidically to the oxygen atom in $OR^{21}$, $OR^{24}$, $OR^{25}$ or $OR^{26}$; or
   (ii) at least one of $R^{10}$, $R^{12}$ and $COR^5$ is an ester group in which the alcohol moiety is a glycosidic group.

5. The method according to claim 3, wherein said $OR^{21}$, $OR^{24}$, $OR^{25}$ and $OR^{26}$ are O-β-D-glucosidyl; and at least one of $R^{10}$, $R^{12}$ and $COR^5$ is an ester group in which the alcohol moiety is a glycosidyl group selected from the group consisting of O-α-D-glucosidyl, O-β-D-galactosidyl, O-α-L-arabinosidyl and O-β-D-xylosidyl.

6. The method according to claim 4, wherein said $OR^{21}$, $OR^{24}$, $OR^{25}$ and $OR^{26}$ are O-β-D-glucosidyl; or at least one of $R^{10}$, $R^{12}$ and $COR^5$ is an ester group in which the alcohol moiety is a glycosidyl group consisting of O-α-D-glucosidyl, O-β-D-galactosidyl, O-α-L-arabinosidyl and O-β-D-xylosidyl.

7. The method according to claim 1, wherein the gibberellin is selected from the group consisting of $GA_1$-3-O-β-D-glucoside, $GA_1$-13-O-β-D-glucoside, $GA_3$-3-O-β-D-glucoside, $GA_3$-13-O-β-D-glucoside, $GA_3$-3,13-di-O-β-D-glucoside, $GA_4$-3-O-β-D-glucoside, $GA_7$-3-O-β-D-glucoside, $GA_{19}$-13-O-β-D-glucoside, $GA_{20}$-13-O-β-D-glucoside, $GA_{30}$-12-O-β-D-glucoside and $GA_{53}$-13-O-β-D-glucoside and gibberellin D-glucosidyl esters of $GA_1$, $GA_3$, $GA_4$, $GA_7$, $GA_9$, $GA_{19}$, $GA_{20}$, $GA_{30}$ and $GA_{53}$, ($GA_1$-D-glucosyl ester, $GA_3$-D-glucosyl ester, $GA_4$-D-glucosyl ester, $GA_7$-D-glucosyl ester, $GA_9$-D-glucosyl ester, $GA_{19}$-D-glucosyl ester, $GA_{20}$-D-glucosyl ester, $GA_{30}$-D-glucosyl ester and $GA_{53}$-D-glucosyl ester).

8. The method according claim 1, wherein $R^7$ is OH; and $R^{10}$ is —O—$R^{23}$, and wherein $R^{23}$ together with $R^4$ forms a lactone ring.

9. The method according claim 1, wherein $R^7$ is OH; and $R^{10}$ is —O—$R^{23}$, and wherein $R^{23}$ together with $R^4$ forms a lactone ring and wherein $R^1$ and $R^2$ together form a double bond, or $R^2$ and $R^3$ together form a double bond.

10. The method according to claim 1, wherein $R^8$ is OH; and $R^{10}$ is —O—$R^{23}$, and wherein $R^{23}$ together with $R^4$ forms a lactone ring.

11. The method according to claim 1, wherein $R^8$ is OH; and $R^{10}$ is —O—$R^{23}$, where $R^{23}$ together with $R^4$ forms a lactone ring and wherein $R^1$ and $R^2$ together form a double bond; or $R^2$ and $R^3$ together form a double bond.

12. The method according to claim 1, wherein $R^{10}$ is —O—$R^{23}$, and wherein $R^{23}$ together with $R^4$ forms a lactone ring.

13. The method according to claim 1, wherein $R^{10}$ is —O—$R^{23}$, where $R^{23}$ together with $R^4$ forms a lactone ring, and wherein $R^1$ and $R^2$ together form a double bond; or $R^2$ and $R^3$ together form a double bond.

14. The method according to claim 1, wherein $R^7$ is H or OH.

15. The method according to claim 1, wherein $R^7$ is H or OH, and $R^1$ is H; $R^2$ is H; and $R^3$ is H or OH.

16. The method according to claim 1, wherein $R^{11}$ is absent; and $R^{12}$ is $CH_3$.

17. The method according to claims 1, wherein $R^{11}$ is absent; and $R^{12}$ is $CH_3$, and $R^{10}$ and $R^1$ together form a double bond, or $R^1$ and $R^2$ together form a double bond; or $R^2$ and $R^3$ together form a double bond.

18. The method according to claim 1, wherein said gibberellin compound is selected from the group consisting of $GA_1$, 3-oxo-$GA_1$, $GA_2$, $GA_3$, 3-oxo-$GA_3$, $GA_4$, $GA_5$, $GA_6$, $GA_7$, $GA_8$, $GA_9$, $GA_{12}$-aldehyde, $GA_{12}$, 12α-OH $GA_{12}$, 12α-OH $GA_{14}$, $GA_{14}$-aldehyde, $GA_{14}$, $GA_{15}$, 12α-OH $GA_{15}$, $GA_{18}$, $GA_{18}$-aldehyde, $GA_{19}$, $GA_{20}$, $GA_{21}$, $GA_{22}$, $GA_{23}$, $GA_{24}$, $GA_{26}$, $GA_{30}$, $GA_{31}$, $GA_{32}$, $GA_{33}$, $GA_{34}$, $GA_{35}$, $GA_{36}$, 12α-OH $GA_{37}$, $GA_{37}$, $GA_{38}$, $GA_{44}$, $GA_{47}$, $GA_{48}$, $GA_{49}$, $GA_{50}$, $GA_{53}$-aldehyde, $GA_{53}$, $GA_{54}$, $GA_{55}$, $GA_{56}$, $GA_{57}$, $GA_{58}$, $GA_{59}$, $GA_{60}$, $GA_{67}$, $GA_{68}$, $GA_{69}$, $GA_{70}$, $GA_{71}$, and $GA_{72}$, and glycosidic ethers and glycosidic esters thereof.

19. The method according to claim 1, wherein the compound is selected from the group of gibberellins consisting of $GA_1$, $GA_3$, $GA_4$, $GA_9$, $GA_{19}$, $GA_{20}$, $GA_{53}$ and $GA_{12}$-aldehyde and glycosidic ethers and glycosidic esters thereof.

20. The method of claim 1, wherein said gibberellin compound blocks the enzyme 5-α-reductase that normally converts testosterone to dihydrotestosterone.

* * * * *